United States Patent [19]

Sauer et al.

[11] Patent Number: 5,882,937
[45] Date of Patent: Mar. 16, 1999

[54] AMMONIA MONITOR

[75] Inventors: Richard L. Sauer, League City, Tex.; James R. Akse; John O. Thompson, both of Roseburg, Oreg.; James E. Atwater, Eugene, Oreg.

[73] Assignee: The United States of America as represented by the Administrator of the National Aeronautics and Space Administration, Washington, D.C.

[21] Appl. No.: 903,279

[22] Filed: Jul. 9, 1997

Related U.S. Application Data

[60] Provisional application No. 60/022,526 Jul. 10, 1996.

[51] Int. Cl.$^6$ ............................ G01N 33/00; G01N 27/00
[52] U.S. Cl. .................. 436/113; 422/82.01; 422/82.02; 436/106; 436/108; 436/111; 436/150; 436/163; 436/175; 436/178
[58] Field of Search ................. 422/68.1, 81, 82.01, 422/82.02; 436/113, 106, 108, 111, 149, 150, 151, 174, 175, 177, 178, 183, 163

[56] References Cited

U.S. PATENT DOCUMENTS

| | | | |
|---|---|---|---|
| 3,545,931 | 12/1970 | McKinley, Jr. | 436/113 |
| 3,718,433 | 2/1973 | Emmet | 23/230 R |
| 3,765,841 | 10/1973 | Paulson et al. | 23/230 R |
| 4,209,299 | 6/1980 | Carlson | 23/230 R |
| 4,268,279 | 5/1981 | Shindo et al. | 95/46 |
| 4,314,824 | 2/1982 | Hansen et al. | 23/230 R |
| 4,700,709 | 10/1987 | Kraig | 128/635 |
| 5,158,868 | 10/1992 | Bergkuist et al. | 435/4 |

FOREIGN PATENT DOCUMENTS

| | | | |
|---|---|---|---|
| 3842068 | 6/1990 | Germany | 439/113 |
| 4211907 | 11/1992 | Germany . | |
| 5-126791 | 5/1993 | Japan . | |

OTHER PUBLICATIONS

T. Tanaka et al., *Kankyo Gijutsu* 1986, 15, 544–547.
U. Spohn et al., *Fresenius Z Anal. Chem.* 1989, 332, 849–854.

*Primary Examiner*—Arlen Soderquist
*Attorney, Agent, or Firm*—Hardie R. Barr

[57] ABSTRACT

Ammonia monitor and method of use are disclosed. A continuous, real-time determination of the concentration of ammonia in an aqueous process stream is possible over a wide dynamic range of concentrations. No reagents are required because pH is controlled by an in-line solid-phase base. Ammonia is selectively transported across a membrane from the process stream to an analytical stream under pH control. The specific electrical conductance of the analytical stream is measured and used to determine the concentration of ammonia.

20 Claims, 7 Drawing Sheets

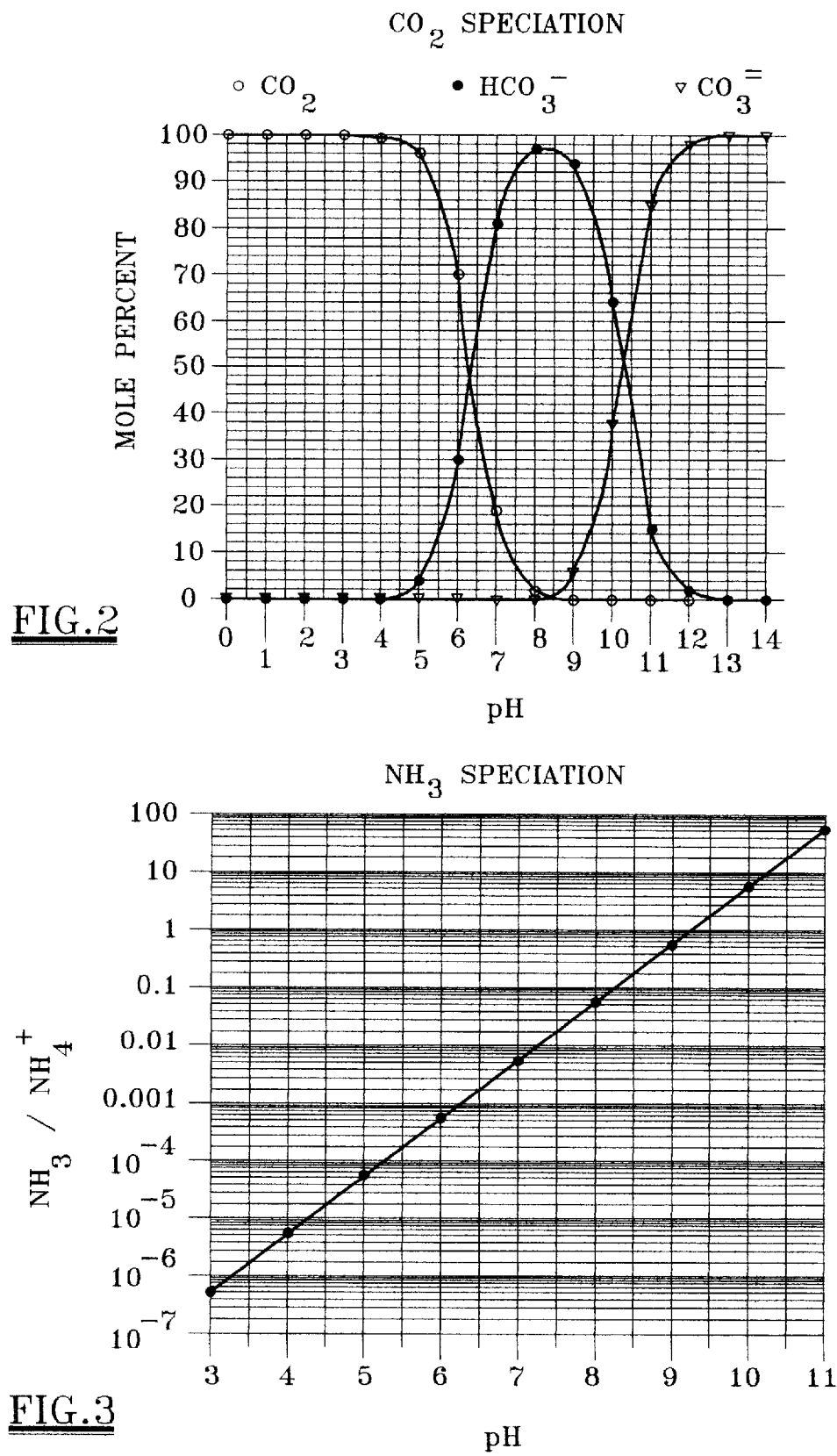

AMMONIA MONITOR

STATEMENT AS TO RIGHTS TO INVENTIONS MADE UNDER FEDERALLY SPONSORED RESEARCH AND DEVELOPMENT

The invention described herein was made in the performance of work under a NASA contract and is subject to the provisions of Section 305 of the National Aeronautics and Space Act of 1958, Public Law 85-568 (72 Stat. 435; 42 U.S.C. 2457).

CROSS-REFERENCE TO RELATED APPLICATION

The invention described herein was described in a Provisional Patent Application, application Ser. No.: 60/022,526; filed: Jul. 10, 1996.

BACKGROUND OF THE INVENTION

1. Field of the Invention

Real time, on-line detection and quantitation of aqueous ammonia is a critical requirement for closed loop environmental life support systems. Dissolved ammonia and the ammonium cation are primarily of biogenic origin, resulting from the metabolic degradation of nitrogenous biomolecules such as amino acids, purines, and pyrimidines. The predominant hydrophilic metabolite, urea, is unstable with respect to hydrolysis and readily decomposes to ammonia and carbon dioxide. Hence, accurate and timely characterization of ammonia levels in closed loop reclamation streams is required to ensure proper water processor operation.

Conventional analytical techniques are generally unsuitable for continuous ammonia monitoring due to sample conditioning requirements, measurement instability, interferences, discontinuous aliquot sampling, and slow response times. For example, calorimetric determinations such as Nesslerization, or the phenate method require sample conditioning as well as reaction with chromogenic reagents. Ion chromatography requires the addition of a buffer and can only analyze selected aliquots whose interval depends on the time needed for separation and elution of ionic constituents. Ammonia ion selective electrodes require pH adjustment and the presence of ionic strength adjusting buffers, need frequent recalibration, suffer from slow response at low concentrations, and can become unstable due to contamination of the ammonia permeable membrane which then must be replaced. Although some of these techniques can be adapted to quasi-real time operation, the added cost and complexity makes them unattractive.

2. Description of Related Art Including Information Disclosed Under 37 C.F.R. 1.97 and 1.98

The subject invention was made as a real time, online detection and quantitation system for aqueous ammonia for use in a closed loop environmental life support system. However, it may be used in any aqueous process stream for detection and quantitation of ammonia.

The following references relate to detection and measurement of ammonia in liquids.

U.S. Pat. No. 4,700,709 to Kraig discloses an apparatus for determining the concentration of ammonium ion in fluid or tissue without adjusting the pH thereof, the apparatus comprising (a) an ammonia concentration measuring electrode for contacting the fluid or tissue and producing a first output signal related to ammonia concentration therein, (b) a hydrogen ion concentration measuring electrode for contacting the fluid or tissue and producing a second output signal related to hydrogen ion concentration therein, (c) temperature measuring means for contacting the fluid or tissue and producing a third output signal related to temperature therein, and (d) means for calculating ammonium ion concentration based upon the first, second and third output signals utilizing a disclosed equation.

U.S. Pat. No. 4,314,824 to Hansen et al. discloses a method of preparing a sample for treatment in which a continuous flow of liquid carrier receives sample portions, the method comprising: passing the carrier through a conduit in a manner such that flow of the carrier is laminar, unsegmented and continuous; introducing sample portions into the carrier; controlling dispersion of the sample portion in the carrier by varying at least one of the volume of the sample portion, the flow velocity of the carrier, or the dimensions of the conduit conducting the sample and the carrier. Also disclosed is an apparatus for practicing the method.

U.S. Pat. No. 3,718,433 to Emmet discloses a process for determining in an aqueous sample the content of nitrogen containing compounds from the group consisting of urea and tyrosine, through chemical reaction and spectral absorbency determination. The process comprises: (1) mixing the aqueous sample at a pH between 4.0 and 8.0 with a solution containing free chlorine; (2) mixing the resultant solution between a pH of 8.0 and 11.0 with a phenol solution; (3) determining the absorbency of the resultant solution substantially in the 454 $\mu$ and in the 375 $\mu$ region of the spectrum; and (4) comparing the resultant absorbency of step 3 at 454 mu with a standard urea sample, and the resultant absorbency of step 3 at 375 mu with a standard tyrosine sample.

U.S. Pat. No. 4,209,299 to Carlson discloses a method for determining the amount of volatile electrolyte present in an aqueous liquid sample, comprising: transferring volatile electrolyte from the sample into a second liquid of known electrical conductivity through a gas-permeable hydrophobic membrane that does not pass the aqueous liquid, during a predetermined time interval, and then determining the change in electrical conductivity in the second liquid resulting from such transfer. The invention also discloses an apparatus for practicing the method.

U.S. Pat. No. 5,158,868 to Bergkuist et al. discloses a method for measuring a constituent of interest of a biological fluid or the like comprising the steps of: providing a reaction chamber that contains an immobilized enzyme capable of modifying a constituent of interest; providing a measuring system; placing a first portion of a biological fluid to be analyzed in the reaction chamber and concurrently exposing a second unmodified portion of the biological fluid to the measuring system to provide a first data output; oscillating the first biological fluid portion with bidirectional flow in the reaction chamber to facilitate modification by the immobilized enzyme of the constituent of interest in the biological fluid; then exposing the first portion of the biological fluid to be analyzed to the measuring system to provide a second data output; and modifying the second data output as a function of the first data output to provide an indication of the actual amount of the constituent of interest in the biological fluid. The invention also discloses a detecting means that comprises an ion selective electrode and a reference electrode.

U.S. Pat. No. 3,765,841 to Paulson et al. discloses a method for determining the concentration of a component in a sample, wherein the sample, upon being introduced into solution with a reagent, reacts therewith at a rate indicative of the concentration. The method comprises: monitoring a characteristic of the solution or a component or product of the reaction which is proportional to the concentration; generating an output signal proportional to the time rate of change of the characteristic; measuring the value of the output signal; and inhibiting the measurement of the value of the output signal for a predetermined, fixed time interval from introduction of the sample into the reagent, the time interval being sufficient to permit thorough mixing of the sample with the reagent. Also disclosed is an apparatus for practicing the method.

SUMMARY OF THE INVENTION

The invention is a real time, on-line system and method for the detection and quantitation of aqueous ammonia in a closed loop environmental life support system. More specifically, it is a system in which on-line pH conditioning takes place through the incorporation of solid phase acid (SPA) and/or solid phase base (SPB) beds into a process stream, the separation and detection takes place on a continuous, real time basis with an adjustable response time through use of a liquid—liquid exchange module(LLEM), and an ammonia monitor allows the on-line detection of NH3 and $NH_4+$ species in the concentration range of 10 ug/L to 20 mg/L in solutions whose pH ranges between 4.5 and 8.5, and which contain a volatile potential interference from $CO_2$.

Broadly, in one aspect, the present invention provides a method for detecting ammonia in an aqueous process stream. The method includes:

(a) contacting the aqueous process stream with a solid phase base to obtain a conditioned stream with a substantially constant pH;

(b) selectively transporting any ammonia in the conditioned stream into an aqueous analytical stream;

(c) detecting the ammonia in the analytical stream.

The analytical stream and the conditioned stream in step (b) flow along opposite sides of a microporous, hydrophobic gas permeable membrane. The membrane in step (b) is preferably in the form of hollow tubes.

BRIEF DESCRIPTION OF THE DRAWINGS

FIG. 2 is a graph showing $CO_2$ speciation as a function of pH in terms of the percent carbon between $CO_2$ (○—○—○), $HCO_3^-$ (●—●—●) and $CO_3^=$ (▽—▽—▽).

FIG. 3 is a graph of $NH_3$ speciation as a function of pH in terms of the ratio of $NH_3$ to $NH_4^+$ on a logarithmic scale.

DESCRIPTION OF THE PREFERRED EMBODIMENTS

The invention allows real time separation and detection of ammonia and eliminates many of the problems present in conventional forms of analysis. The technology disclosed herein involves, principally, the performance of three major sequential steps in which five sub-processes are accomplished. An overview of one particular embodiment of the technology is shown schematically in FIG. 1. Initially those volatile species such as carbon dioxide which may interfere with the later selective segregation of ammonia are eliminated. The second step uses a liquid—liquid exchange across a vapor channel in a microporous membrane to equilibrate the ammonia level of the process stream with that in the analytical stream. Significantly, these first two steps are moderated by pH conditioning which occurs via equilibrium dissolution of a solid phase acid or a solid phase base placed in-line with the process stream being measured. In both cases, membrane separation is used for segregation of chemical species. The final step is either a conductometric or electrochemical detection of ammonia in the analytical stream. This technique provides a reliable, interference free method of ammonia detection and quantitation.

Figure 1:
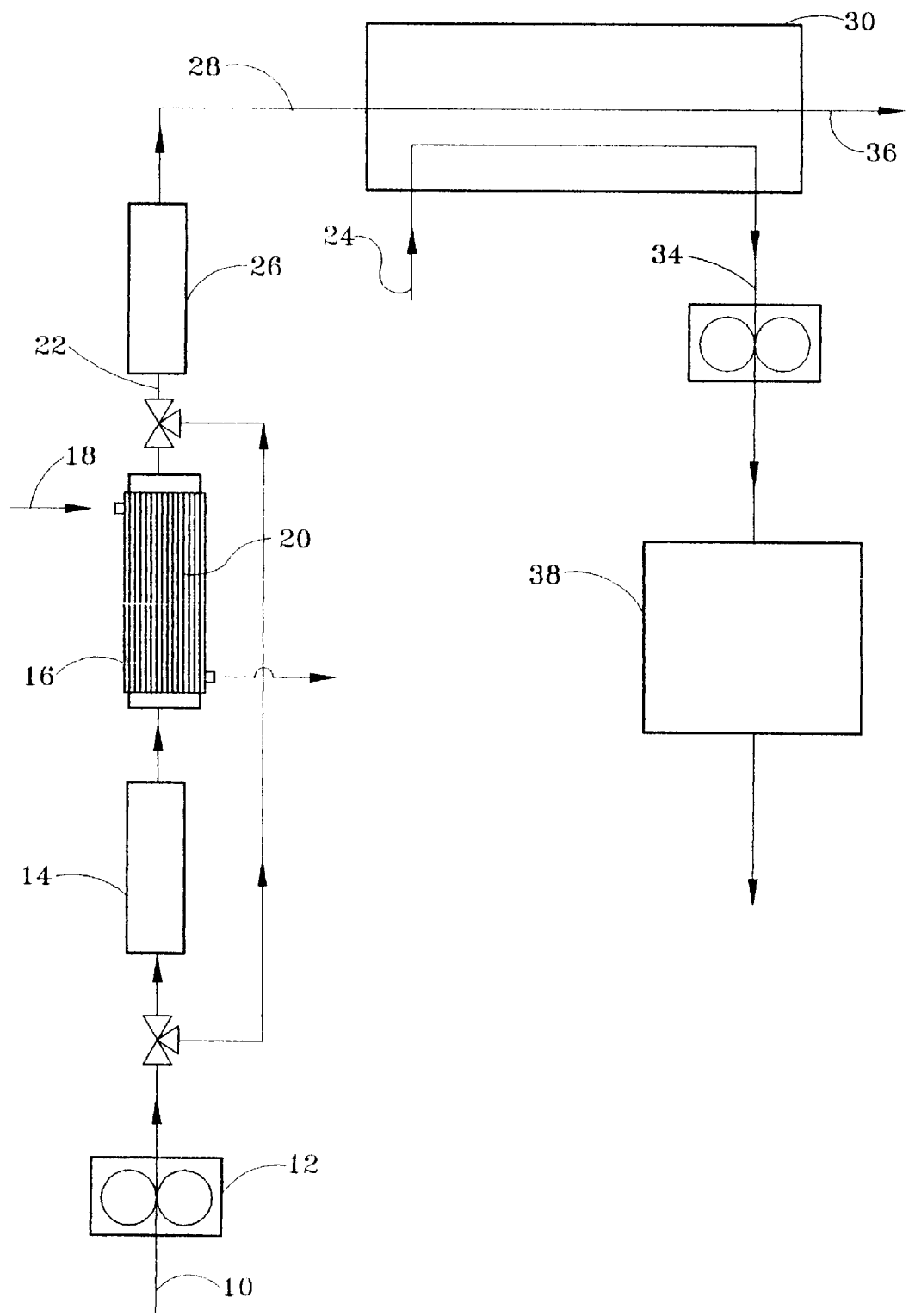
FIG. 1 is a schematic drawing of an integrated ammonia monitor according to the principles of the present invention.

With reference to FIG. 1, the process stream 10 is initially passed via pump 12 through the solid phase acid (SPA) bed 14. The purpose of the bed 14 is to enhance the volatility of purgable, acidic chemical species such as carbon dioxide, acetates, sulfur dioxide, nitrogen oxides and others which might later interfere with ammonia detection. The method used for this purpose is pH control. In the case of the SPA bed 14, an effluent pH of 3.25±0.25 is achieved for a variety of influents provided that sufficiently long contact times are allowed. At this pH nearly all carbonate and bicarbonate species will be converted to carbon dioxide as shown in FIG. 2. At a pH below 5, the solubility of carbon dioxide is given by Henry's Law, $P_i = k_i X_i$, where $P_i$ is partial pressure of $CO_2$, $k_i$ is the Henry's Law constant, and $X_i$ is the mole fraction of CO in solution. The Henry's Law constant as a function of temperature is given by:

$$k_{i,CO2} = (55.556)*\exp(-6789.04T - 11.4519*\ln T - 0.10454*T + 94.4914)$$

where T is in degrees Kelvin.[2] With air containing 300 ppm of carbon dioxide the amount of $CO_2$ remaining in solution at equilibrium is 0.462 mg/L demonstrating that extremely low levels of carbon dioxide can be achieved under equilibrium conditions. These conditions are reached prior to the gas-liquid separator (GLS) 16 where the supersaturated carbon dioxide will be eliminated.

The GLS 16 removes the dissolved $CO_2$ by transferring it across a microporous, hydrophobic, polypropylene gas permeable membrane to $CO_2$ free purge gas stream 18. Since the pH is low, ammonia will remain in solution as $NH_4^+$ as shown in FIG. 3. This membrane is in the form of small hollow tubes 20. Such a unit is very permeable to gases due to the high surface porosity, high surface to volume ratio, and short diffusion distances. Due to the small pore size (0.05 $\mu$m) and hydrophobicity, these tubes can support high internal pressures before water is forced through the pores. According to the equation of Young and Laplace, $\Delta P = 2\gamma \cos\theta/r$ where $\Delta P$ is differential pressure, $\gamma$ is the surface free energy for a water-air interface, $\theta$ is the contact angle for a water droplet on polypropylene, and r is the equivalent pore radius, the membrane can support a differential pressure of 258 psi. The purge gas of choice is nitrogen due to its low $CO_2$ content although other gases with low $CO_2$ levels can also be used.

Figure 4:
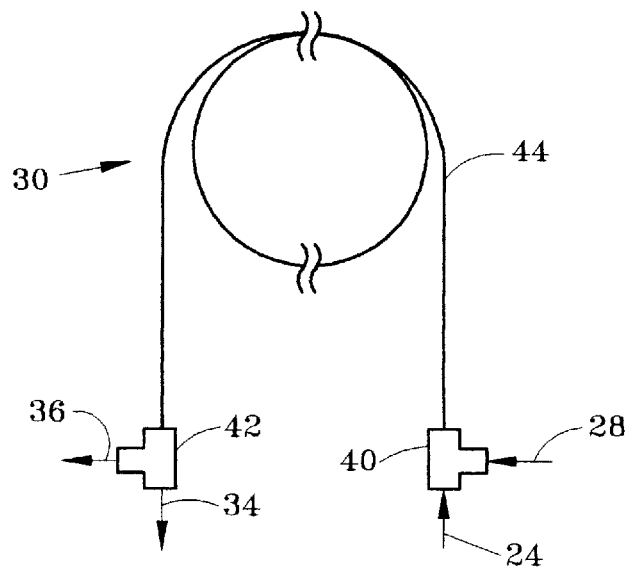
FIG. 4 is a schematic diagram which can be used in the ammonia monitor of FIG. 1.
Figure 4B:
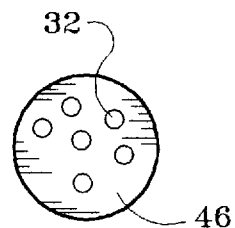
FIG. 4b is a cross sectional view of the face of the epoxy plug used in the inlet of the liquid-liquid exchange module of FIG. 4a as seen along the lines 4b–4b.
Figure 4A:
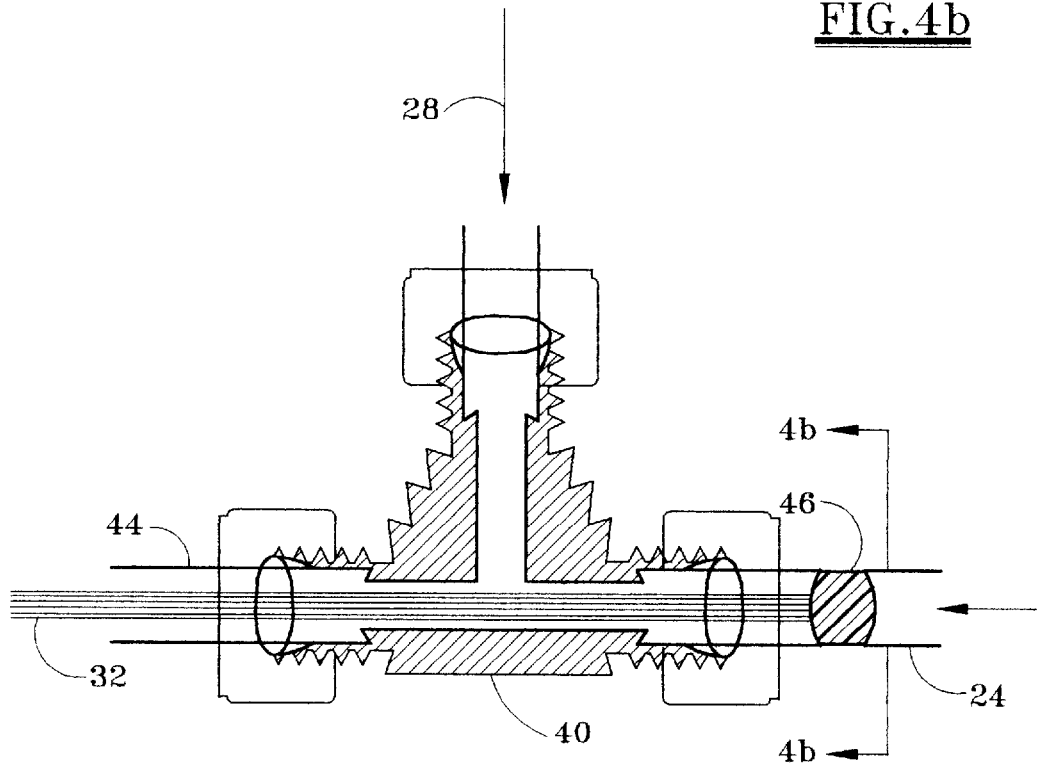
FIG. 4a is a schematic diagram of the inlet of the liquid—liquid exchange module of FIG. 4.

The second step is the transfer of ammonia in the conditioned acidified, degassed process stream 22 to the analytical stream 24. In order to initiate this step, the pH of the process stream 22 must first be raised so that $NH_4^+$ is converted to its volatile form, $NH_3$. The solid phase base (SPB) bed 26 accomplishes this task by raising the pH for a variety of challenge solutions to 10.00±0.25. Even though the transfer membrane is identical to that in the GLS 16, the nature of the transfer of $NH_3$ from the process stream 28 to the analytical stream 24 in the liquid—liquid exchange module (LLEM) 30 which is shown in FIGS. 4, 4a and 4b is markedly different than the $CO_2$ removal process. $NH_3$ is first transferred from the aqueous process stream 28 into the trapped gas phase within the process of the membrane, and then to the aqueous analytical stream 24 on the other side of the membrane 32. If an attempt was made to purge $NH_3$ from an aqueous stream into air, the process would be extremely slow due to the very low value of Henry's Law constant for ammonia which is given by $k_{i,NH3}=(55.556)*\exp(-157.552/T+28.1001*\ln T-0.049227*T-149.006)$ and is ~1750 times lower than that for CO. This low value means that $NH_3$ is much more stable in the aqueous phase than in the gas phase, and consequently, only an extremely small quantity of gas phase $NH_3$ is present at equilibrium. As a result, the $NH_3$ transfer rate is controlled by the diffusional flux in the gas phase which is dominated by two terms, the $NH_3$ chemical potential gradient and the transport distance. Both of these terms are improved dramatically when transport occurs between two aqueous streams rather than from an aqueous stream to the gas phase. In the first place, the transport distance in the gaseous medium is narrowed to the length of the pore rather than from the surface of the liquid to some unspecified distance away from the surface of the membrane. Secondly, the analytical stream 24 initially acts as an $NH_3$ sink via $NH_4^+$ which increases the chemical potential gradient and drives the transport. Consequently, the transfer process will be dominated by geometric considerations such as the high surface area to volume ratio within tubular membranes 32, the short gas phase diffusion distances, and the mass transfer zone length (i.e. LLEM 30 length).[4,5] With the properly designed LLEM 30, the $NH_3$ content in the analytical stream 34 will be identical to that in the process stream 28. Alternatively, by changing the geometry and flow conditions, the $NH_3$ concentration of the analytical stream 34 can be adjusted for maximum sensitivity or for minimum response time.

Figure 5:
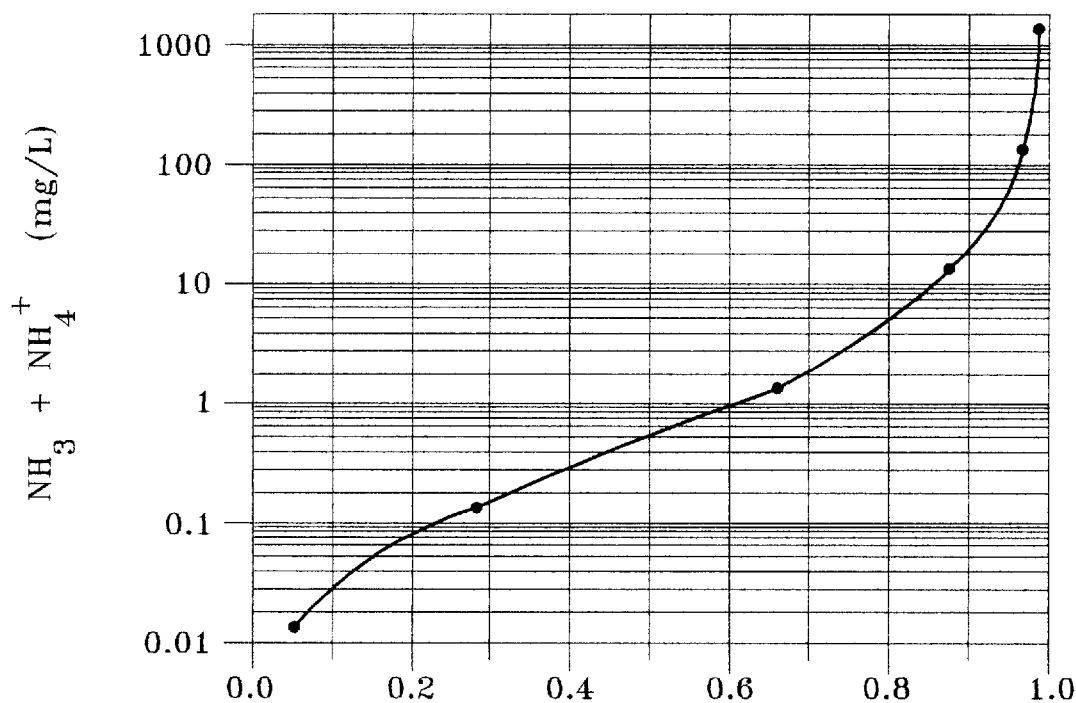
FIG. 5 is a graph showing unbuffered $NH_3$ speciation as a function of the ratio of $NH_3$ to the sum of $NH_3$ and $NH_4^+$ in terms of the total concentration of $NH_3$ and $NH_4^+$ species on a logarithmic scale.

The final step in the analysis is the detection of the ammonia in the analytical stream 34. The speciation of ammonia as a function of concentration in unbuffered water as shown in FIG. 5 indicates that the relative concentration of $NH_4^+$ available for conductivity detection should be more than adequate over the concentration range of 0.1 to 20 mg/L. Since non-volatile species are not transferred to the analytical stream 34, the detection of $NH_3$ is made much easier due to the absence of most interferences. Conductivity is a particularly attractive detection technique due to its simplicity and reliability. The most likely interfering chemical species which are transferable under basic conditions and which have ionic forms are organonitrogen compounds such as amines, amides, and imines. This should be a fairly limited list due to the aqueous solubilities, speciation, volatilities, and Henry's Law constant for these species.

Additional details regarding the LLEM 30 are illustrated in FIGS. 4, 4a and 4b. The LLEM 30 includes inlet tee 40 and outlet tee 42 which are connected by an outer tubing 44 which can be provided in the form of a coil as illustrated in FIG. 4. The inlet tee 40, which is similar in construction to the outlet tee 42, is illustrated in FIG. 4a to show that the process stream 28 is introduced via the side connection to the tee 40 and that the tubular membranes 32 pass through the straight continuous portion of the tee 40. On the downstream side of the tee 40, the tubular membranes 32 generally run colinearly with the outer tubing 44. On the connection at the other side of the tee 40, the tubular membranes 32 pass through a plug 46 in fluid communication upstream with the analytical stream 24 (see FIG. 4b).

This new approach to real time, on-line ammonia monitoring has a number of distinct advantages over conventional alternatives. Foremost among these is the separation and detection on a continuous, real time basis with an adjustable response time. Secondly, the complete separation of the analytical stream 24 from the process stream 28 reduces the complexity and improves the reliability of the detection scheme since virtually no secondary chemical species will be present to foul, alter, or in any way change the response of the detector 38. Another feature is the passive control of the pH of the process stream through the equilibrium dissolution in the SPA and SPB beds. Included in the attributes of these pH beds is the relatively low concentration of chemical additives required to adjust the pH. In fact, for those cases where the SPB bed is used alone, the amount of contamination added to the stream in the form of metal ions is well below the NASA potable water specifications.

There are three novel features of this technology. One is the incorporation of the SPA and/or SPB beds into the process stream for on-line pH conditioning. These beds allow good control of the pH even in the presence of other chemical species. The second is the design of the LLEM which provides greater efficiency and controllability for $NH_3$ transport. The third is the combination of these devices in the ammonia monitor which allows the on-line detection of $NH_3$ and $NH_4^+$ species in the concentration range of 40 $\mu$g/L to 20 mg/L in solutions whose pH ranges between 4.5 and 8.5, and which contain a volatile potential interference from $CO_2$.

Solid phase acids and bases are a reliable and effective means for pH control. The equilibrium dissolution from the SPA or SPB beds 14 and 26 can produce acidic pH's of 3.25±0.25 or basic pH's of 10.0±0.20. These values are only moderately influenced by the pH of the influent streams 10, 22. The primary factors which determine how closely the equilibrium pH value is approached are the contact time of the solution with the bed (i.e. kinetics), the temperature, and the composition of the challenge solution. The volatility of both $CO_2$ and $NH_3$ in the process streams 22 and 28, respectively is readily controlled at the pH of the SPA and SPB beds 14 and 26. In addition, the speciation of $CO_2$ and $NH_3$ as a function of pH allows the segregation of one from the other. This segregation can also occur with only the SPB bed 26 in place since $CO_2$ species remain in solution under basic conditions. Such an arrangement would minimize the amount of expendables required for system maintenance.

The equilibrium pH for the SPA bed 14, when challenged with distilled water, is 3.25. Table 1 shows the behavior of the bed 14 when challenged by 5.6 to 20.7 mg/L of $NH_4Cl$, and 1.6 to 28.0 mg/L of $(NH_4)_2CO_3$. The data show that the inlet pH of 4.7 to 5.2 for $NH_4Cl$ is lowered to values between 3.1 and 3.2 after passage through the bed 14, while the inlet pH of 6.0 to 8.2 for $(NH_4)CO_3$'s is lowered to values between 3.2 and 3.4. In both cases, at these effluent pH's, the equilibrium value of the dissolved carbonate species consists solely of dissolved $CO_2$ in accordance with Henry's Law, and consequently, the total inorganic carbon remaining in solution is extremely small.

TABLE 1

Solid Phase Acid Module Performance

| $(NH_4)_2CO_3$ mg/L | $NH_4Cl$ mg/L | Influent pH | Effluent pH |
|---|---|---|---|
| 1.57 | — | 5.97 | 3.17 |
| 2.80 | — | 6.20 | 3.15 |
| 27.96 | — | 8.26 | 3.48 |
| — | 5.63 | 5.17 | 3.09 |
| — | 20.73 | 4.74 | 3.15 |

The SPB bed 26 was challenged with the acid solutions. This Bed 26 normally produces a pH of 10.0 when challenged with distilled water under equilibrium conditions. The results from the acidic challenge are shown in Table 2. The effluent pH was raised from the influent range of 3.0 to 3.5 to a consistent value between 9.8 and 10.2 with the lower pH's occurring at higher total $NH_4^+$ concentrations. This makes sense if one considers that in order to purge one mole of $NH_4^+$ from the process stream, one mole of $OH^-$ must react with $NH_4^+$ to form $H_2O$ and $NH_3$. The lower pH's are due to the elimination of $OH^-$ by this reaction. As previously shown in FIG. 3, $NH_3$ will predominate at this pH. Between 50 and 80% of all ammonia species will be in the purgable $NH_3$ form which over the length of the LLEM 30 will allow a full purging of $NH_3$.

TABLE 2

Solid Phase Base Module Performance

| $(NH_4)_2CO_3$ mg/L | $NH_4Cl$ mg/L | Influent pH | Effluent pH |
|---|---|---|---|
| 0.50 | — | 3.26 | 10.16 |
| 1.75 | — | 3.18 | 10.16 |
| 2.80 | — | 3.20 | 10.10 |
| 27.96 | — | 3.50 | 9.78 |
| — | 0.37 | 3.12 | 10.23 |
| — | 3.23 | 3.13 | 10.19 |
| — | 20.73 | 3.15 | 10.00 |

Figure 6A:
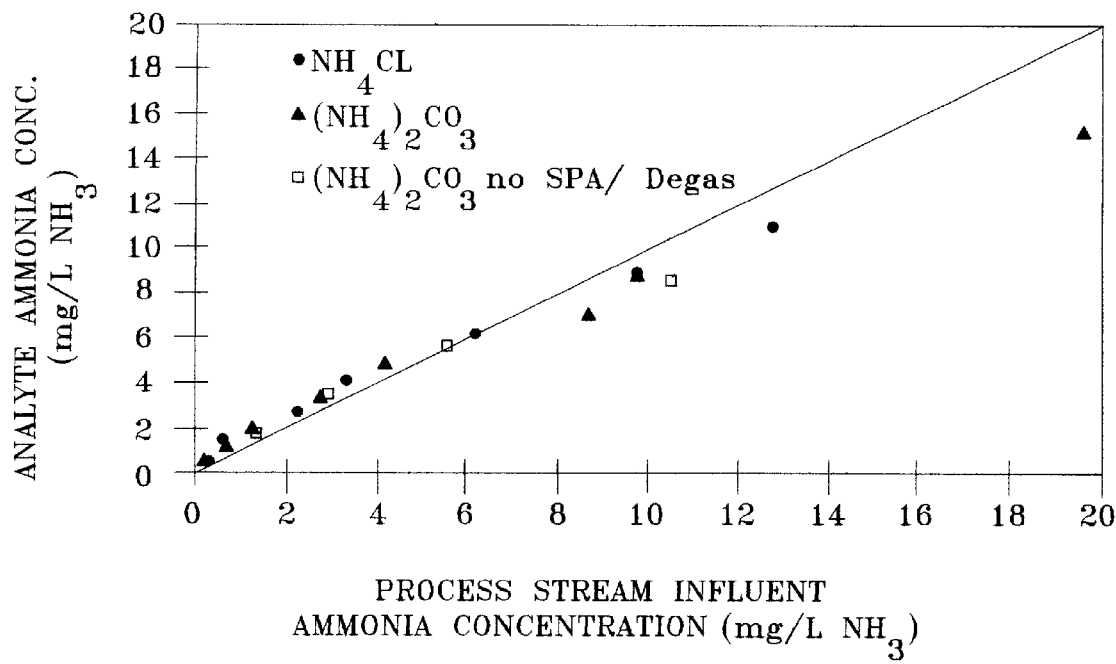
FIG. 6a is a graph showing system ammonia transfer performance of the ammonia monitor of FIG. 1 as a function of the process stream ammonia concentration in terms of the analyte ammonia concentration for process stream ammonia concentrations up to 20 mg/L $NH_3$.
Figure 6B:
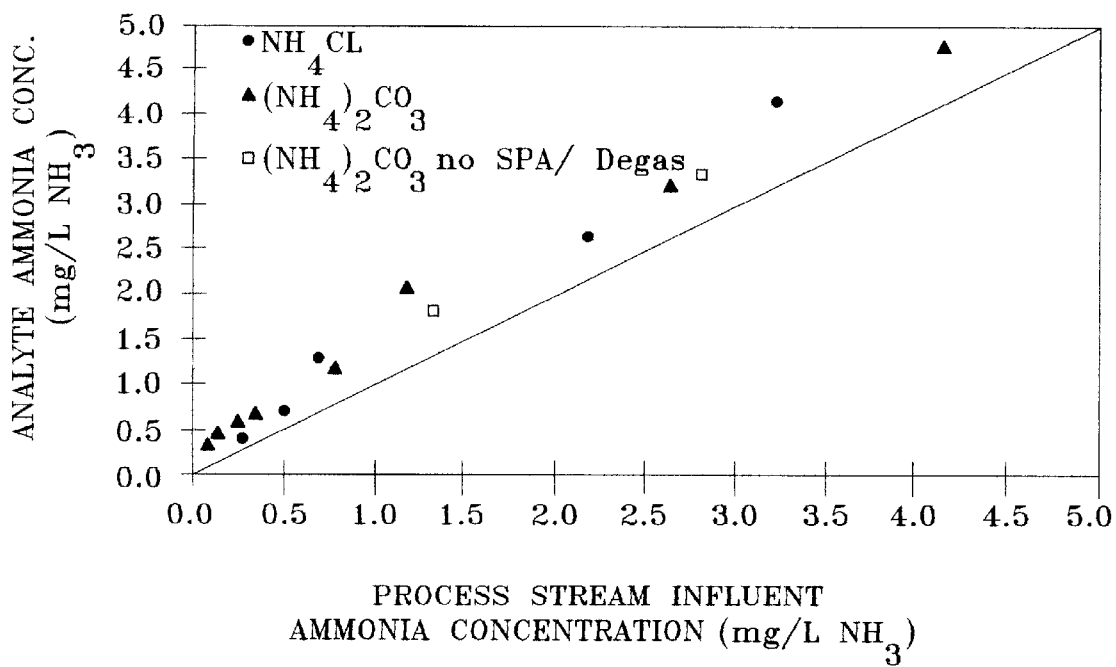
FIG. 6b is a graph of the system ammonia transfer performance of FIG. 6a for the ammonia concentrations over the range from 0 to 5.0 mg/L $NH_3$.

The LLEM 30 was challenged with $NH_3$ concentrations ranging between 0.104 to 19.5 mg/L. The challenges consisted of both $NH_4Cl$ and $(NH_4)_2CO_3$ solutions which were previously run through the SPA bed 14 and the degasser 16 combination, and then through the SPB bed 26. In addition to these acidified solutions which are devoid of $CO_2$, an $(NH_4)_2CO_3$ solution was run without acidification. The flow rate of the process stream was, 5 ml/minute and the flow rate of the analytical stream 24 was 0.22 ml/minute. The two streams flowed co-currently with equal velocities under these flow conditions. The levels of both the process influent stream 28 and analytical effluent stream 34 were analyzed using the Nesslerization technique. The results are shown in FIG. 6.

Figure 7:
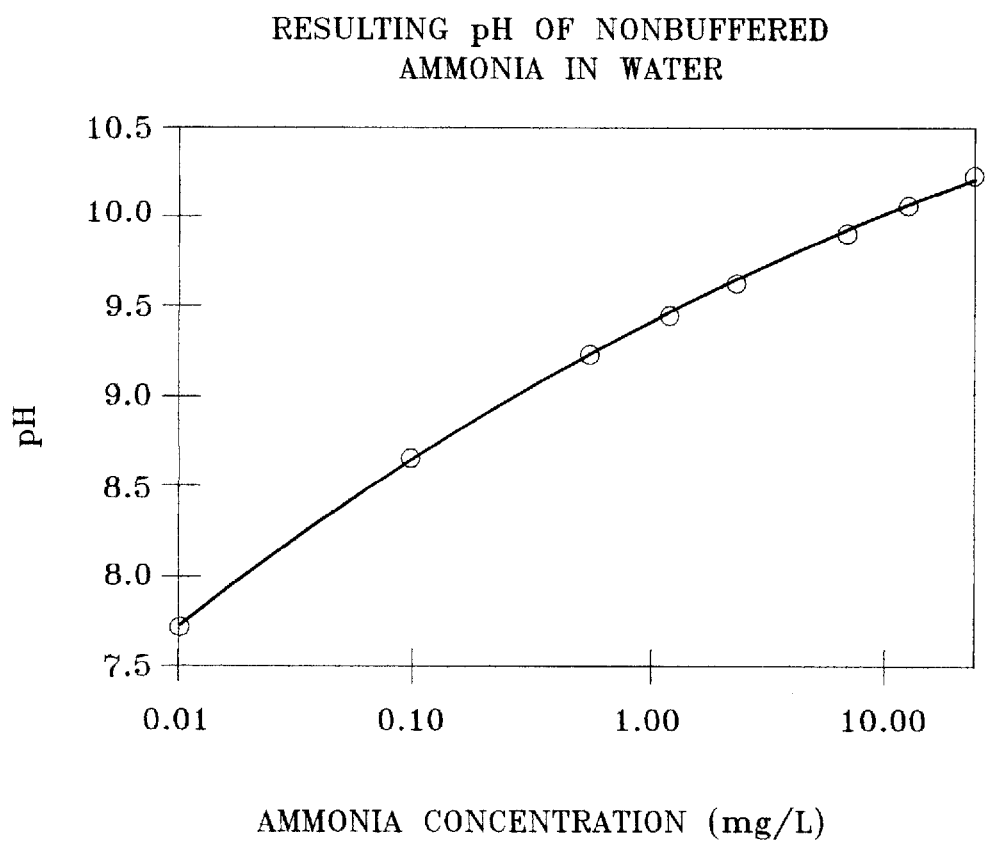
FIG. 7 is a graph showing the resulting pH of non-buffered ammonia in water.

These, data demonstrate the effective exchange of $NH_3$ from process stream 28 to analytical stream 34 in the LLEM 30. In addition, this exchange does not require the prior removal of $CO_2$, $CO_3^=$, or $HCO_3^-$ species indicated by the fact that all data points track the same curve. At concentrations above 6 to 10 mg/L the exchange curve bends over indicating a sub-equilibration of the analytical stream 34 with the process stream 28. There are two likely reasons for this behavior. As the concentration of $NH_3$ increases, the net flux of $NH_3$ across the membrane 32 must also increase, and eventually the transport conditions such as exchange area, concentration gradient, and contact time will no longer support this high flux. A more important contribution to this behavior is the decreasing chemical potential gradient between the two streams at a high $NH_3$ concentration. The available $NH_3$ in the process stream 28 is fixed by the total concentration of all ammonia species, and the pH. This determines the chemical potential of $NH_3$ at the gas-liquid interface of the process stream 28. The pH of analytical stream 34 is not fixed and depends on the concentration of all ammonia species as shown in FIG. 7. As the pH increases with higher $NH_3$ levels, the chemical potential of $NH_3$ at the gas-liquid interface in the analytical stream 34 will be increased. These changes can be calculated from the equilibrium expression for the ammonia-water hydrolysis reaction. For example, regardless of the ammonia concentration in the process stream 28 the buffered pH of 10 requires that 84.9% of all ammonia species will consist of $NH_3$, while in the unbuffered analytical stream 34 a 1 mg/L ammonia solution will contain 58.1% $NH_3$ and a 10 mg/L ammonia solution will contain 84.0% $NH_3$. As can be seen from these values, the driving force for $NH_3$ transport decreases as the total equilibrium concentration increases, and at lower concentrations, the percentage of $NH_3$ available in the process stream 28 will always be higher than in the analytical stream 34. Under such conditions, ammonia can be pumped into the analytical stream 34 until their chemical potentials are equal. This behavior can be manipulated to increase the sensitivity of the technique or conversely to optimize the response time.

Figure 8A:
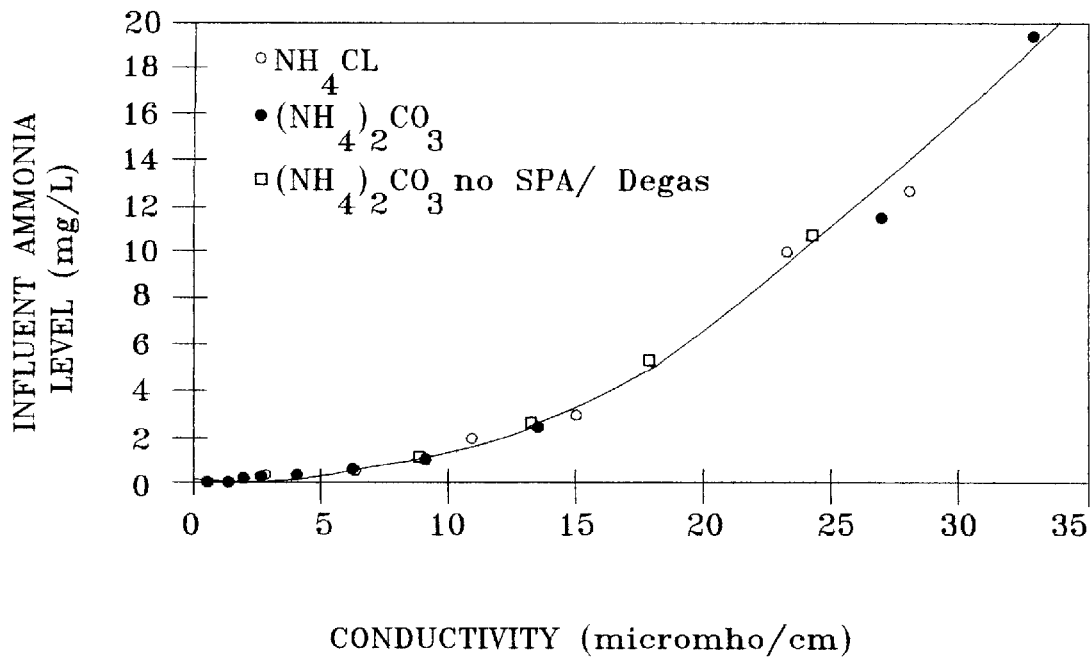
FIG. 8a is a graph showing the correlation of the influent ammonia level in the process stream being analyzed as a function of conductivity where the influent ammonia is in the form of $NH_4Cl$ (○—○—○), $(NH_4)_2CO_3$ (●—●—●) and $(NH_4)_2CO_3$ without SPA bed or other degasification (—).
Figure 8B:
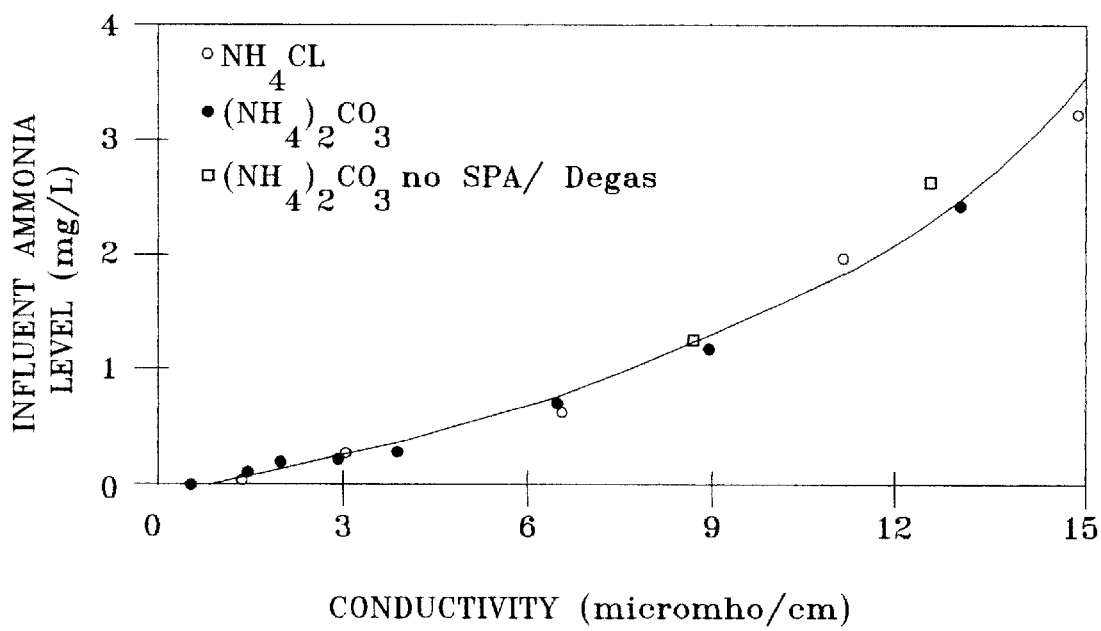
FIG. 8b is an enlarged graph of the influent ammonia concentration versus conductivity of FIG. 8a for conductivities from 0 to 15 micromho/cm.

The complete ammonia monitoring system was challenged with both $(NH_4)_2CO_3$ and $NH_4Cl$ solutions containing $NH_3$ levels between 0.042 and 19.8 mg/L. The results are shown in FIG. 8. The conductivity response curve displays excellent sensitivity over the entire concentration range and little selectivity between the carbonate and chloride ammonium salts. In addition, the same relative response decrease at higher concentrations that was present in the earlier exchange curve is evident. The curvature at low concentrations of $NH_3$ is especially pronounced and is much steeper than in the $NH_3$ exchange curve (see FIG. 7). This response is most probably due to the combined effects of the increasing ratio of $NH_4^+/NH_3$ with dilution and the capacity of the LLEM 30 to concentrate $NH_3$ in the analytical stream at low concentrations where relatively low pHs produce a higher driving force for $NH_3$ exchange. These data follow a smooth curve with little scatter which can be fitted to a quadratic equation given by $[NH_3]$ (mg/L)=$0.0188*\sigma 2$ ($\mu$mho$^{-1}$/cm)$^2$$-0.0490*\sigma(\mu$mho$^{-1}$/cm)$+0.1938$ with a correlation coefficient of $r^2$=0.9936. These measurements were generally taken going from high concentrations to low, with a single $NH_3$ curve, although on occasion, the procedure was changed to fill in data gaps. This response is remarkable since data were generated for different challenge solutions at different times.

We claim:

1. A method for detecting ammonia in an aqueous process stream, comprising the steps of:

(a) contacting the aqueous process stream with a solid phase base to obtain a conditioned stream with a substantially constant pH;

(b) selectively transporting any ammonia in the conditioned stream into an aqueous analytical stream;

(c) detecting the ammonia in the analytical stream.

2. The method of claim 1 wherein the conditioned stream has a pH of about 10.

3. The method of claim 2 wherein the pH of the conditioned stream is 10±0.25.

4. The method of claim 1 further comprising the step of preconditioning the aqueous process stream by (i) contacting the process stream with a solid phase acid to obtain an acidic process stream with a pH of 3.25±0.25 and (ii) separating volatile gases from the acidic process stream to obtain a preconditioned stream for supply to step (a).

5. The method of claim 4 wherein the separation step (ii) comprises transferring $CO_2$ across a microporous, hydrophobic gas permeable membrane to a purge gas essentially free of $CO_2$.

6. The method of claim 1 wherein the analytical stream in step (b) comprises distilled water.

7. The method of claim 6 wherein the analytical stream and conditioned stream in step (b) flow either co-currently or preferentially counter-currently along opposite sides of a microporous, hydrophobic gas permeable membrane.

8. The method of claim 7 wherein the membrane comprises hollow tubes and the analytical stream is passed through the tubes at a substantially equal velocity with the conditioned stream flowing around the tubes.

9. The method of claim 1 wherein the ammonia concentration in the analytical stream from step (b) approximates the ammonia concentration of the conditioned steam supplied to step (b).

10. The method of claim 1 wherein the ammonia detection step (c) comprises measuring electrical conductivity of the analytical stream from step (b) as an indication of ammonia content.

11. The method of claim 1 wherein the ammonia detection step comprises measuring pH of the analytical stream from step (b) as an indication of ammonia content.

12. The method of claim 1 wherein steps (a), (b) and (c) are continuous.

13. Apparatus for detecting ammonia in an aqueous process stream comprising:

a bed of solid phase base for continuous passage of the process stream therethrough to obtain a conditioned process stream with a substantially constant pH;

a liquid—liquid exchange module including a microporous, hydrophobic gas permeable membrane for selectively transporting ammonia from the conditioned process stream into an analytical stream to obtain an analytical stream effluent containing ammonia;

means for detecting the ammonia in the analytical stream effluent.

14. The apparatus of claim 13 wherein the solid phase base bed produces a conditioned process stream with a pH of 10.0±0.25.

15. The apparatus of claim 13 further comprising:

a bed of solid phase acid upstream of the solid phase base bed for acidifying the process stream to a pH of 3.25±0.25; and a gas-liquid separator form removing dissolved gases from the acidified process stream before passage of the process stream through the solid phase base bed.

16. The apparatus of claim 15 wherein the gas-liquid separator comprises a microporous, hydrophobic gas permeable membrane and a purge gas stream essentially free of $CO_2$ on a side of the membrane opposite the acidified process stream.

17. The apparatus of claim 13 wherein the membrane in the liquid—liquid exchange module comprises a plurality of hollow tubes disposed colinearly in a larger outer tube.

18. The apparatus of claim 17 wherein the liquid—liquid exchange module comprises an inlet and outlet for the process streams adjacent opposite ends of the outer tube, and wherein the hollow tubes pass through a plug at either end of the outer tube.

19. The apparatus of claim 13 wherein the ammonia detection means comprises a conductivity cell for measuring the specific electrical conductivity of the analytical stream effluent.

20. The apparatus of claim 13 wherein the ammonia detection means comprises a pH mode for measuring the pH of the analytical stream effluent.

* * * * *